United States Patent [19]

Atwood et al.

[11] Patent Number: 5,695,333
[45] Date of Patent: Dec. 9, 1997

[54] DENTAL ARTICULATOR APPARATUS

[75] Inventors: Michael O. Atwood, 110 Wessex Way, Folsom, Calif. 95630; Jerry S. Hansen, Pollock Pines, Calif.

[73] Assignee: Michael O. Atwood, Folsom, Calif.

[21] Appl. No.: 641,888

[22] Filed: May 2, 1996

[51] Int. Cl.⁶ .................... A61C 11/02; A61C 11/06
[52] U.S. Cl. .................... 433/57; 433/56; 433/59; 433/60
[58] Field of Search .................. 433/59, 56, 60, 433/55, 57, 54

[56] References Cited

U.S. PATENT DOCUMENTS

| | | | |
|---|---|---|---|
| 1,319,737 | 10/1919 | Wadsworth | 433/59 |
| 1,906,797 | 5/1933 | Lentz | 433/57 |
| 2,070,025 | 2/1937 | Phillips | 433/57 |
| 3,510,947 | 5/1970 | Tuccillo et al. | 433/60 |
| 4,319,875 | 3/1982 | Beckwith | 433/60 |
| 5,141,433 | 8/1992 | Peterson | 433/57 X |

*Primary Examiner*—Jeffrey A. Smith
*Attorney, Agent, or Firm*—Thomas R. Lampe

[57] ABSTRACT

Dental articulator apparatus includes an articulator base, a post extending upwardly from the articulator base, and an upper articulator member movably mounted on the post. The apparatus incorporates upper and lower dental cast or mold supports which allow the molds to be snapped in place on the apparatus or readily removed therefrom. The apparatus also includes an incisal guide member support connected to the base and extending outwardly therefrom between the upper articulator member and the articulator base. The incisal guide member support has a number of incisal guide member support sides alternatively presented for engagement by an incisal guide member depending from the upper articulator member.

18 Claims, 5 Drawing Sheets

DENTAL ARTICULATOR APPARATUS

TECHNICAL FIELD

This invention relates to an articulator for supporting dental molds or casts.

BACKGROUND ART

Dental articulators are employed to hold dental casts and are for the purpose of simulating the structure and operation of a patient's upper jaw and lower jaw and teeth when working on dental casts or models, the later typically being constructed of stone, plaster and the like. Articulators are employed in the fabrication of all dental appliances, such as dentures, partials, crowns and bridges. Dental offices and laboratories employ articulators throughout the process required to create the final appliance. The appliance is created outside the patient's mouth in a dental laboratory.

Prior art articulators are often characterized by their relative complexity. Furthermore, prior art articulators do not readily lend themselves to manual support by an individual performing work on the dental casts or models attached to the articulator. Adjustment of conventional articulators can be a time consuming process. In general, articulators present an unattractive appearance and are relatively unwieldy due do to both configuration and size thereof.

DISCLOSURE OF INVENTION

The present invention relates to dental articulator apparatus which is characterized by its relative simplicity and low expense as compared to comparable prior art articulators. Furthermore, the articulator apparatus of the present invention incorporates a number of features which contribute to the ease and convenience of operation thereof when employing the apparatus to perform work on dental molds or models. Furthermore, the dental articulator apparatus of the present invention is of relatively compact and employs a configuration which facilitates usage thereof.

The dental articulator apparatus of the present invention includes an articulator base and an upper articulator member support attached to the articulator base and extending upwardly from the articulator base.

An upper articulator member is movably mounted on the upper articulator member support and extends over the articulator base. The upper articulator member defines a cavity receiving the upper articulator member support and the upper articulator member includes upper articulator member portions disposed on opposed sides of the upper articulator member support.

A lower dental cast support is mounted on the articulator base and projects upwardly therefrom. An upper dental cast support is mounted on the upper articulator member and projects downwardly therefrom.

At least one of the dental cast supports includes a support element connected to the remainder of the dental articulator apparatus by a snap fastener.

An incisal guide member is adjustably connected to the upper articulator member and extends downwardly from the upper articulator member between the upper articulator member support and the upper cast support.

An incisal guide member support is connected to the upper articulator member support and extends outwardly therefrom between the upper articulator member and the articulator base. The incisal guide member support is engageable by the incisal guide member to support the incisal guide member. The incisal guide member support is selectively movably mounted on the upper articulator member support and includes a plurality of incisal guide member support sides alternatively presented for engagement by the incisal guide member upon movement of the incisal guide member support relative to the upper articulator member support.

Other features, advantages, and objects of the present invention will become apparent with reference to the following description and accompanying drawings.

BEST MODE FOR CARRYING OUT THE INVENTION

Figure 1:
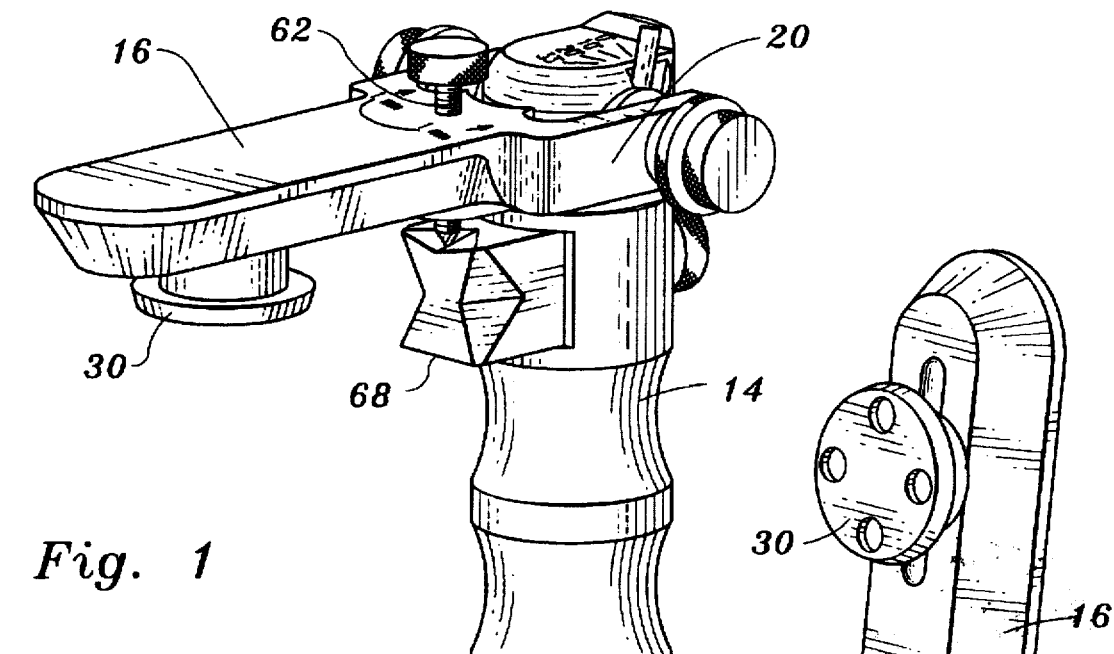
FIG. 1 is a perspective view of dental articulator apparatus constructed in accordance with the teachings of the present invention, with the upper articulator member in lowered position.
Figure 3:
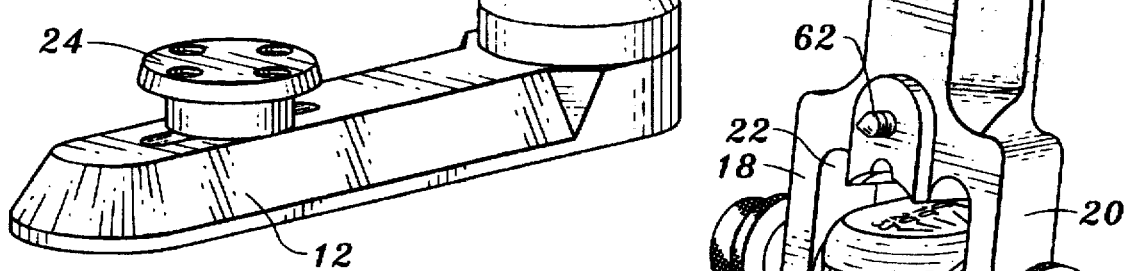
FIG. 3 is a front view of the incisal guide member support of the present invention as depicted by arrows 3 in FIG. 2.
Figure 3:
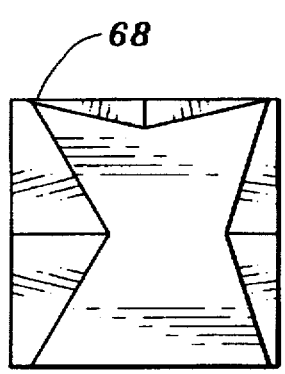

Referring to the drawings, dental articulator apparatus constructed in accordance with the teachings of the present invention includes an articulator base 12 having a flat bottom for positioning on a level surface.

An upper articulator member support in the form of a single post or column 14 sized and configured for manual grasping by an individual is attached to and extends upwardly from the articulator base.

Figure 2:
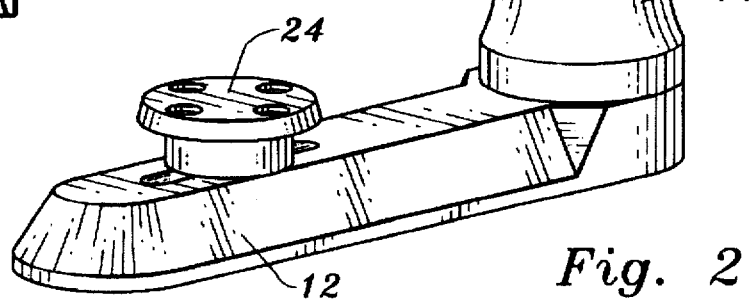
FIG. 2 is a view similar to FIG. 1 but illustrating the upper articulator member in raised position.
Figure 4:
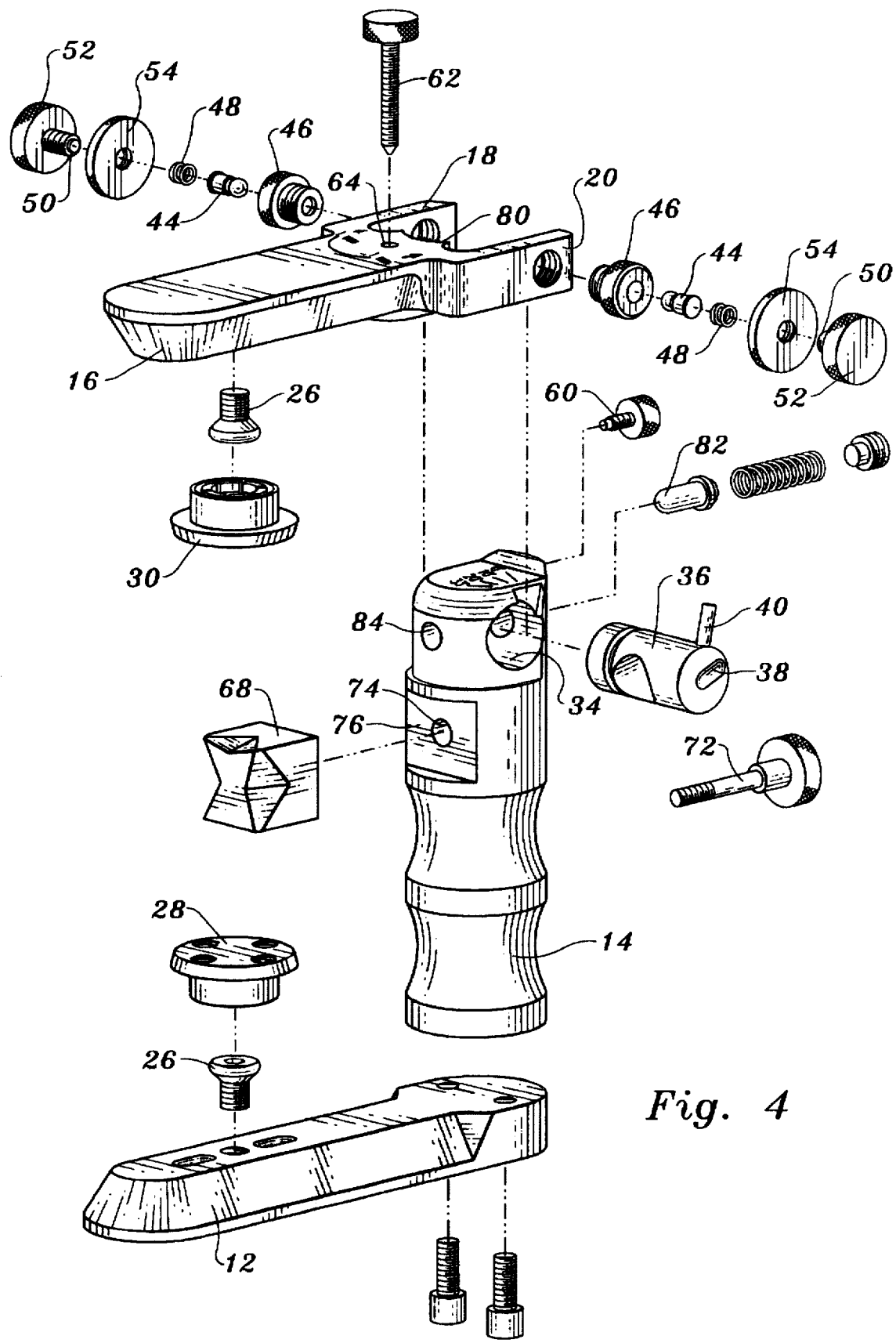
FIG. 4 is an exploded view of the dental articulator apparatus.

An upper articulator member 16 is movably mounted on the post 14 in a manner which will be described in greater detail below and extends over the articulator base 12 when the upper articulator member is generally parallel thereto as shown in FIG. 1. FIG. 2 illustrates the upper articulator member 16 pivoted to a position where it is disposed substantially 90 degrees relative to the articulator base. One end of the upper articulator member is bifurcated, having spaced fork legs 18, 20 disposed on opposite sides of the post 14 and defining a cavity 22 accommodating the post.

A lower dental cast or mold support 24 is mounted on the articulator base and projects upwardly therefrom. Support 24 includes two support elements, one support element comprising a screw 26 having an enlarged head and threadedly engaged with the articulator base and a second support element 28 which may be suitably comprised of rubber or plastic and is snap fit over the enlarged head of screw 26 to maintain the support elements together. In operation, support element 28 is molded into the bottom of the dental mold or casting which is to be positioned on articulator base 12. Thus, the lower mold or casting may readily be removed from or snap fastened into place with respect to the articulator base as desired. This is to be contrasted with the typical prior art approach wherein threaded fasteners are employed to connect the mold in position on the articulator.

An upper dental cast support 30 of like construction is mounted on the upper articulator member and projects downwardly therefrom. The upper cast or mold may be readily separated from or snap fastened to the upper articulator member. In various figures of the drawings; namely, FIGS. 5–11, the upper and lower dental molds or castings are depicted by dash lines.

A throughbore or opening 34 passes through post 14 at the upper end thereof. Rotatably mounted within opening 34 is condylar guide means in the form of a condylar cylinder 36. Cylinder 36 has opposed outer surfaces defining condylar guide slots 38. The condylar guide slots 38 are identically oriented, it being appreciated that rotation of the cylinder 36 will result in both of the guide slots being identically reoriented relative to the post. A handle 40 on the condylar cylinder is manually graspable by a user to rotate the condylar cylinder and reorient the guide slots as desired.

Connector means interconnects the fork legs 18, 20 of the upper articulator member to the condylar cylinder 36. With respect to each fork leg, the connector means includes a detent member 44 which is axially slidably positioned within the interior of bushing 46 threadedly secured to the fork legs. A compression spring 48 bears against each detent member 44 and urges the same toward the condylar cylinder.

A threaded shaft 50 having a handle 52 thereon is threadedly engaged with the interior of the bushing 46 and is for the purpose of adjusting the compression of the spring. It will be appreciated that such structure not only maintains the detent member ends in the condylar guide slots but can be employed to adjust the horizontal placement of the upper articulator member relative to the post. A lock nut 54 is threadedly secured to threaded shaft 50 to selectively lock the shaft in the desired position.

Rotation of handle 40, as previously stated, results in changes in the orientation of condylar guide slots 38. This in turn will result in different paths of movement of the detent members 44 in the slots when force is applied to the upper articulator member 16 to displace it relative to the post. The condylar structure just discussed is the articulator equivalent of the patient's glenoid fossa and articular space eminence.

Figure 5:
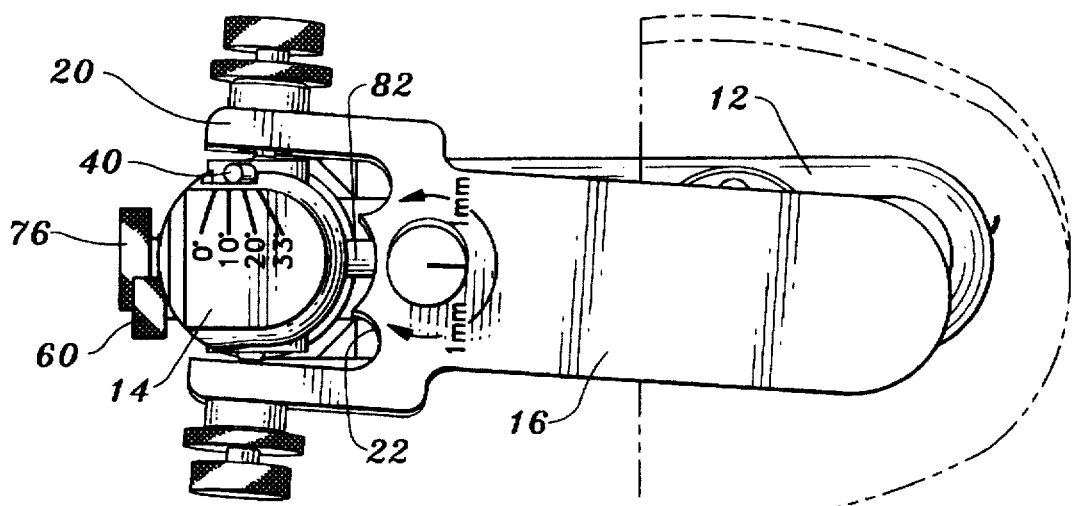
FIGS. 5 through 7 are top plan views of the dental articulator apparatus illustrating the upper articulator member in alternate positions.
Figure 6:
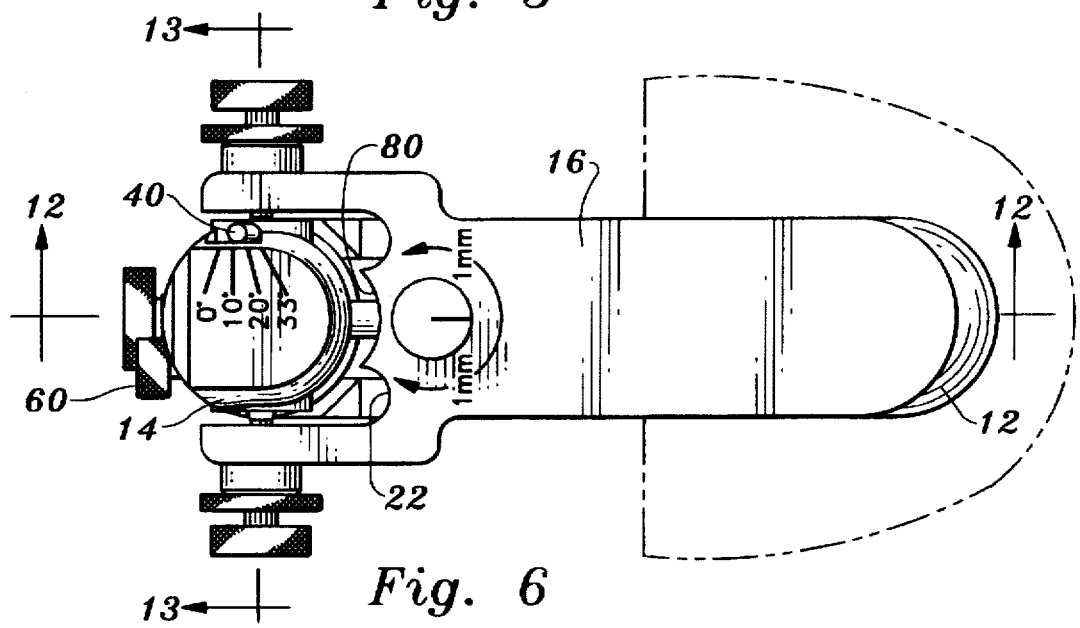
Figure 7:
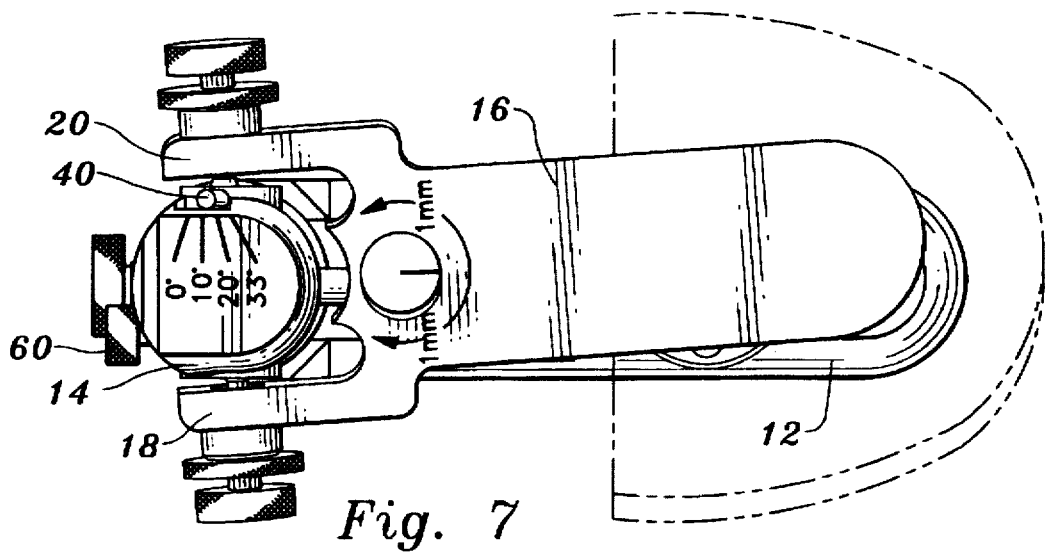
Figure 10:
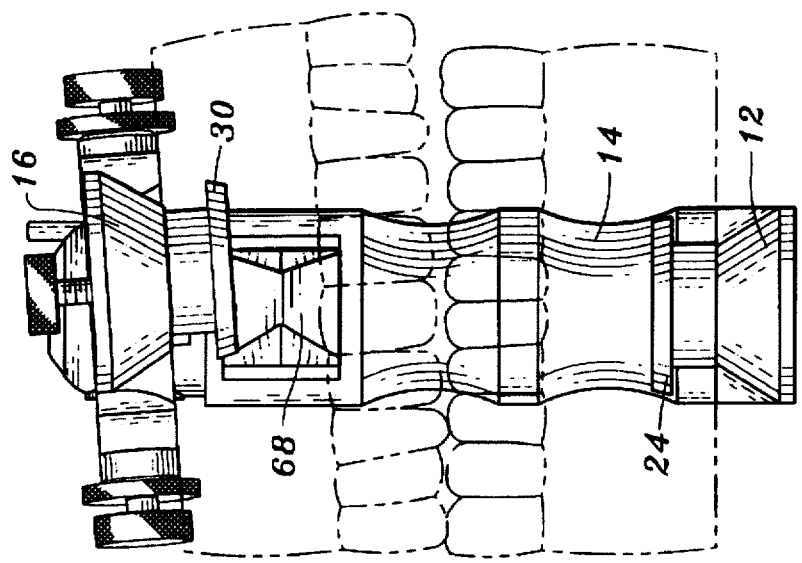
FIGS. 8 through 10 are front elevation views of the dental articulator apparatus illustrating selected structural components thereof in alternate positions.
Figure 9:
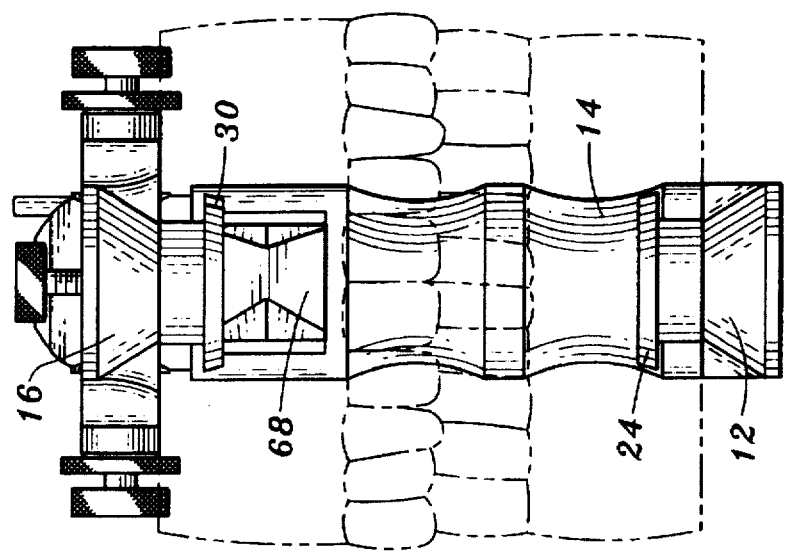

Indicia is provided on the top of post 14 which is for the purpose of showing the angle at which the guide slots are inclined to the horizontal plane. In FIGS. 5–7, for example, the condylar cylinder handle 40 is in registry with the indicia indicating a 10 degree angle. A lock screw 60 is threadedly secured to post 14 and is engageable with the condylar cylinder 36 to selectively lock it at the desired location.

The apparatus also includes an incisal guide member in the form of a threaded elongated pin or shaft 62 which is located in a threaded hole 64 formed in the upper articulator member 16 and has a pointed distal end. Pin 62 extends downwardly from the upper articulator member between the above-described upper articulator member support and the upper cast support. Pin 62 is closely adjacent to post 14. This is to be contrasted with prior art arrangements wherein incisal guide pins are typically located at or near the distal ends of the upper articulator member. Not only is this prior art location awkward, it requires significant rotation of the pin to effect adjustment. A knob is located at the top of the pin for rotating the pin and thus moving it up or down relative to the upper articulator member. In the arrangement illustrated it is desirable that one full turn of the pin will move it up or down one millimeter and indicia is provided on the top of the upper articulator member to indicate this.

Disposed under incisal guide member 62 is an incisal guide member support 68. Incisal guide member support 68 has a threaded opening 70 at the back end thereof which receives the threaded end of a locking bolt 72 passing through a throughbore 74 formed in post 14. The portion of the post 14 surrounding throughbore 74 at the front of the post is machined flat to provide a groove 76 in the post which accommodates and is sized to conform to the shape of incisal guide member support 68. When the locking bolt 72 is tightened the incisal guide member support 68 is locked into position in the groove and cannot rotate.

The incisal guide member support 68 has four incisal guide member support sides alternatively presented for engagement by the incisal guide member upon movement of the incisal guide member support relative to the upper articulator member support. In the arrangement shown, three of the sides are machined to provide sloping converging walls, the walls having differing configurations and slopes. The incisal guide member support may be readily rotated to present alternate sides thereof to the incisal guide member merely by loosening the locking bolt 72, manually rotating the incisal guide member support, and retightening the locking bolt. Change of the orientation of incisal guide member support 68 will usually occur in conjunction with adjustment of the condylar cylinder and condylar guide slots as previously described, the object of course being to reproduce or mimic the patient's jaw movement.

Figure 8:
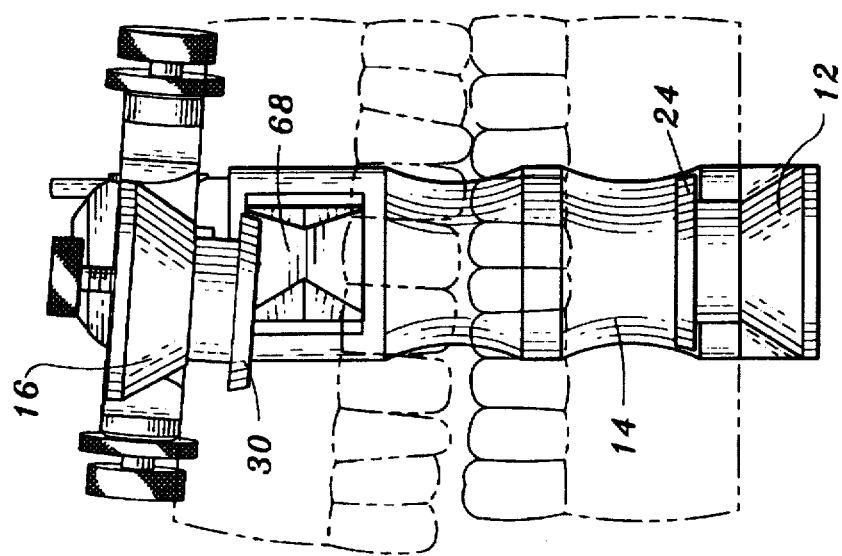
Figure 11:
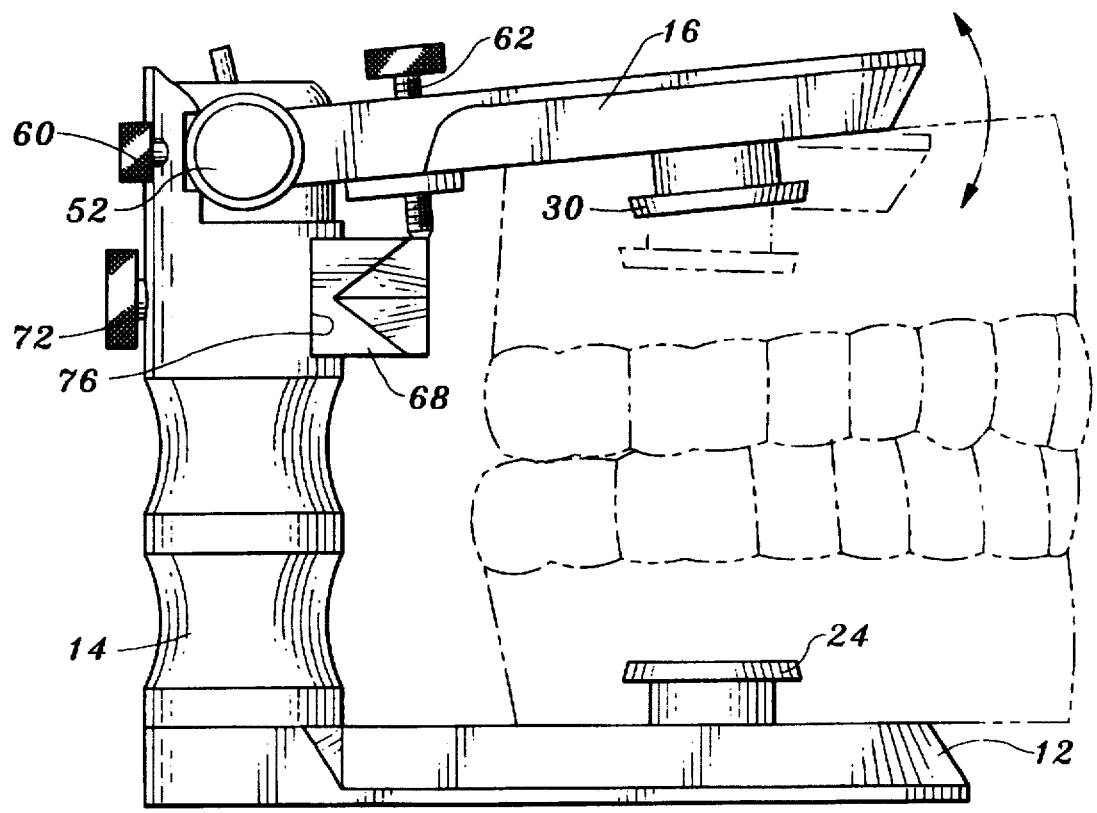
FIG. 11 is a side view of the dental articulator apparatus illustrating alternate positions assumed by the upper articulator member and upper dental cast support in relation to upper and lower dental casts or models employed in association with the apparatus.
Figure 12:
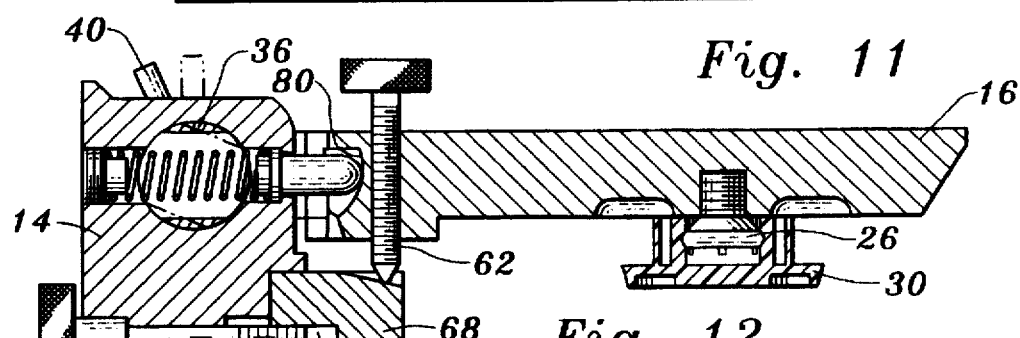
FIG. 12 is a cross sectional view of a portion of the apparatus taken along line 12—12 in FIG. 6.
Figure 13:
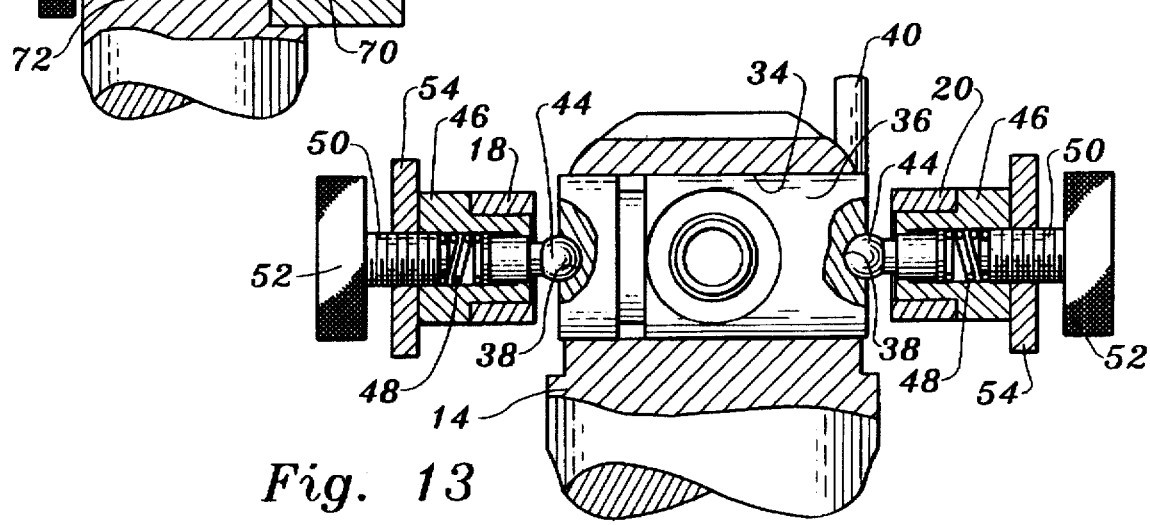
FIG. 13 is an enlarged, cross sectional view of a portion of the apparatus taken along the line 13—13 of FIG. 6.

FIGS. 5 through 10 show representative different relative positions assumed by the structural elements of the dental articulator apparatus. FIGS. 5 and 8 depict one such relative position, FIGS 6 and 9 another, and FIGS 7 and 10 yet another.

In FIGS. 5, 7, 8 and 10 there has been lateral displacement of the upper articulator member 16 relative to the articulator base 12. Means is provided in the apparatus for resisting such lateral displacement. In particular, upper articulator member 16 defines a curved cam surface 80 between fork legs 18, 20. A spring-biased cam follower 82 projects from a hole 84 in post 14 and engages the cam surface 80. Such an arrangement will tend to center the upper articulator member 16.

The apparatus disclosed herein is in the nature of a semi-adjustable articulator; however, it will be appreciated that the principles of the invention are also applicable to fully adjustable articulators. Suitable changes may be made in the structure without departing from the spirit or scope of the invention. For example, the condylar cylinder may be longer than that illustrated and project a significant distance from the sides of the post.

We claim:

1. Dental articulator apparatus comprising, in combination:

an articulator base;

an upper articulator member support attached to said articulator base and extending upwardly from said articulator base;

an upper articulator member movably mounted on said upper articulator member support and extending over said articulator base, said upper articulator member defining a cavity receiving said upper articulator member support and said upper articulator member including upper articulator member portions disposed on opposed sides of said upper articulator member support;

a lower dental cast support mounted on said articulator base and projecting upwardly therefrom;

an upper dental cast support mounted on said upper articulator member and projecting downwardly therefrom;

an incisal guide member adjustably connected to said upper articulator member and extending downwardly from said upper articulator member between said upper articulator member support and said upper cast support; and an incisal guide member support connected to said upper articulator member support and extending outwardly therefrom between said upper articulator member and said articulator base, said incisal guide member support being engageable by said incisal guide member to support said incisal guide member, said incisal guide member support being selectively movably mounted on said upper articulator member support and including a plurality of incisal guide member support sides alternatively presented for engagement by said incisal guide member upon movement of said incisal guide member support relative to said upper articulator member support.

2. The dental articulator apparatus according to claim 1 wherein at least one of said dental cast supports includes first and second support elements, one of said support elements being directly connected to either said articulator base or said upper articulator member and the other of said support elements being directly connectable to a dental casting, and releasable connector means releasably interconnecting said first and second support elements.

3. The dental articulator apparatus according to claim 2 wherein said releasable connector means comprises a snap fastener.

4. The dental articulator apparatus according to claim 1 additionally comprising incisal guide member support lock means for selectively locking said incisal guide member support against movement relative to said upper articulator member support.

5. The dental articulator apparatus according to claim 1 additionally comprising condylar guide means movably mounted on said upper articulator member support having opposed outer surfaces defining condylar guide slots and connector means extending from said upper articulator member portions, positioned in said condylar guide slots and moveable within said condylar guide slots.

6. The dental articulator apparatus according to claim 5 wherein said upper articulator member support defines an upper articulator member support opening, said condylar guide means being rotatably mounted in said upper articulator member support opening to change the orientation of said condylar guide slots relative to said upper articulator member support.

7. The dental articulator apparatus according to claim 6 wherein said condylar guide means comprises a cylinder rotatably mounted in said upper articulator member support opening.

8. The dental articulator apparatus according to claim 6 additionally comprising manually graspable means connected to said condylar guide means for manually rotating said condylar guide means in said upper articulator member support.

9. The dental articulator apparatus according to claim 5 wherein said connector means includes detent members projecting inwardly from said upper articulator member portions, slidably moveable relative to said upper articulator member portions, and having detent member distal ends, and detent member positioning means urging said detent members toward one another for maintaining said detent member distal ends in said condylar guide slots.

10. The dental articulator apparatus according to claim 9 wherein said detent member positioning means includes spring means continuously biasing said detent members toward one another and adjustment means for varying the pressure exerted against said detent members by said spring means.

11. The dental articulator apparatus according to claim 1 wherein said upper articulator member portions comprise spaced fork legs defining said cavity and disposed on opposite sides of said upper articulator member support.

12. The dental articulator apparatus according to claim 1 additionally comprising means cooperable with said upper articulator member for resisting lateral displacement of said upper articulator member relative to said articulator base.

13. The dental articulator apparatus according to claim 12 wherein said means for resisting lateral displacement of said upper articulator member relative to said articulator base includes a cam member affixed to said upper articulator member defining a cam surface and a spring-biased cam follower element in engagement with said cam surface.

14. The dental articulator apparatus according to claim 1 wherein said upper articulator member support comprises a unitary post sized and configured for manual grasping by a person employing the dental articulator apparatus.

15. The dental articulator apparatus according to claim 1 wherein at least one of said dental cast supports includes a support element connected to the remainder of said dental articulator apparatus by a snap fastener.

16. Dental articulator apparatus comprising, in combination:

an articulator base;

an upper articulator member;

upper articulator member support means extending between said articulator base and said upper articulator member and supporting said upper articulator member for pivotal movement relative to said articulator base;

an incisal guide member adjustably connected to said upper articulator member and extending downwardly from said upper articulator member between said upper articulator member and said articulator base; and an incisal guide member support connected to said upper articulator member support means and extending outwardly therefrom between said upper articulator member and said articulator base, said incisal guide member support being engageable by said incisal guide member, said incisal guide member support being selectively movably mounted on said upper articulator member support means and including a plurality of incisal guide member support sides alternatively presented for engagement by said incisal guide member upon movement of said incisal guide member support relative to said upper articulator member support means.

17. The dental articulator apparatus according to claim 16 additionally comprising incisal guide member support lock means for selectively locking said incisal guide member support against movement relative to said upper articulator member support means.

18. Dental articulator apparatus comprising, in combination:

an articulator base;

an upper articulator member support comprising a single manually graspable post attached to said articulator base, extending upwardly from said articulator base, and having an upper distal end;

an upper articulator member movably mounted on said post at the upper distal end of said post and extending over said articulator base, said upper articulator member defining a cavity receiving said post and said upper articulator member including upper articulator member portions disposed on opposed sides of said post;

a lower dental cast support mounted on said articulator base and projecting upwardly therefrom;

an upper dental cast support mounted on said upper articulator member and projecting downwardly therefrom;

condylar guide means movably mounted on said post having opposed outer surfaces defining condylar guide slots; and connector means extending from said upper articulator member portions, positioned in said condylar guide slots, and moveable within said condylar guide slots, said post defining an upper articulator member support opening extending through said post, and said condylar guide means being rotatably mounted in said support opening in said post to change the orientation of said condylar guide slots relative to said post.

* * * * *